(12) United States Patent
Barrett

(10) Patent No.: US 6,175,779 B1
(45) Date of Patent: Jan. 16, 2001

(54) COMPUTERIZED UNIT DOSE MEDICATION DISPENSING CART

(76) Inventor: J. Todd Barrett, 2029 Silver La., Madison, MS (US) 39110

( * ) Notice: Under 35 U.S.C. 154(b), the term of this patent shall be extended for 0 days.

(21) Appl. No.: 09/162,588

(22) Filed: Sep. 29, 1998

(51) Int. Cl.⁷ .................................................. G06F 17/00
(52) U.S. Cl. .................... 700/242; 700/240; 700/236; 700/244; 700/243; 700/237; 221/2; 221/7
(58) Field of Search .................................. 700/241, 237, 700/231, 232, 235, 242, 236, 221, 222, 216; 221/2, 7, 197

(56) References Cited

U.S. PATENT DOCUMENTS

| Re. 35,743 | 3/1998 | Person . | |
|---|---|---|---|
| D. 363,125 | 10/1995 | Gilchrist . | |
| 4,504,153 | 3/1985 | Schollmeyer et al. . | |
| 4,695,954 | * 9/1987 | Rose | 364/413 |
| 4,785,969 | * 11/1988 | McLaughlin | 221/2 |
| 4,847,764 | 7/1989 | Halvorson . | |
| 5,014,875 | 5/1991 | McLaughline et al. . | |
| 5,016,948 | * 5/1991 | Welch et al. | 312/250 |
| 5,047,948 | 9/1991 | Turner . | |
| 5,213,232 | * 5/1993 | Kraft et al. | 221/277 |
| 5,263,596 | * 11/1993 | Williams | 221/153 |
| 5,292,029 | 3/1994 | Pearson . | |
| 5,314,243 | 5/1994 | McDonald et al. . | |
| 5,377,864 | * 1/1995 | Blechl et al. | 221/2 |
| 5,408,443 | * 4/1995 | Weinberger | 368/10 |
| 5,460,294 | 10/1995 | Williams . | |
| 5,480,062 | 1/1996 | Rogers et al. . | |
| 5,502,944 | 4/1996 | Kraft et al. . | |
| 5,536,084 | 7/1996 | Curtis et al. . | |
| 5,562,232 | * 10/1996 | Pearson | 221/7 |
| 5,657,236 | 8/1997 | Conkright . | |
| 5,703,786 | 12/1997 | Conkright . | |
| 5,713,485 | 2/1998 | Liff et al. . | |
| 5,713,487 | 2/1998 | Coughlin . | |
| 5,883,806 | * 3/1999 | Meador et al. | 364/479.14 |
| 5,905,653 | * 5/1999 | Higham et al. | 364/479.14 |
| 6,019,249 | * 2/2000 | Michael et al. | 221/197 |

OTHER PUBLICATIONS

KVM Technologies, Inc., Envoy Automated Medication System, Good Machine Made Simple!, Advertisement, pp. 1–6.

* cited by examiner

Primary Examiner—Christopher P. Ellis
Assistant Examiner—Michael E Bautler
(74) Attorney, Agent, or Firm—Jones, Walker, Waechter, Poitevent, Carrere & Denegre, L.L.P.

(57) ABSTRACT

A computerized medication dispensing cart and system for dispensing prepackaged unit-dose medications to a patient in a medical facility including a computer system on the cart for storing medication information regarding each patient provided by a pharmacy and a plurality of dispensers on the cart that automatically dispense prepackaged unit dosages of prescribed medications at the request of nursing personnel while making rounds. A separate dispenser on the cart is used to dispense each type of medication. An input device, such as a touch screen monitor, is mounted on the cart to permit nursing personnel to access the medication information regarding the patient and to request that the cart dispense the prescribed medications. A detector is mounted on each dispenser that detects the administration of the medications to the patient and records the time and date that the medications were administered.

16 Claims, 6 Drawing Sheets

COMPUTERIZED UNIT DOSE MEDICATION DISPENSING CART

FIELD OF THE INVENTION

The present invention relates generally to a computerized medication dispensing cart and, more particularly, to a computerized medication dispensing cart having a computer system on the cart for storing medication information regarding each patient downloaded from a pharmacy, a plurality of dispensers on the cart that automatically dispense prescribed medications in prepackaged unit dosages at the request of nursing personnel and a detector on each dispenser for detecting the administration of the medication to the patient in order to update the medication information in the computer system for each patient.

BACKGROUND OF THE INVENTION

The prior art discloses various types of computerized medication dispensing carts used by nursing personnel in medical facilities. The basic objects of these inventions are to improve the documentation of the dispensing of medications, to reduce the errors in the dispensing of medications, to lower the costs associated with the dispensing of medications and to improve the security associated with the dispensing of medications. Such prior art discloses a computerized medication dispensing cart that uses a computer system to assist nursing personnel to view and input medication information regarding a patient while making rounds and to transmit and receive medication information regarding a patient with a pharmacy. The use of a computer system eliminates the need for each nurse to manually document the date and amount of the medication given to each patient and to later enter such information into the patient's records. The computerized medication dispensing cart shown in U.S. Pat. No. 536,084 includes a computer system on the cart which transmits and receives medication information regarding each patient while the nurse is making the rounds permitting the real time transfer of data as the cart is being moved throughout the medical facility. As shown in U.S. Pat. No. 5,314,243, such computerized medication dispensing carts disclosed in the prior art may provide for a plurality of drawers in the housing of the cart that each contain the specific medication to be administered to a patient. For purposes of increased security, the drawers are kept locked as the nurse makes rounds until the particular patient's room is reached. The drawers may be unlocked by the nurse by entering a predetermined access code in order to permit the nurse to remove and administer the medications from the drawer to the patient. Thus, the nurse no longer is required to search a cart loaded with hundreds of medications to administer to a patient. However, nurses and other hospital personnel still must spend a substantial amount of time in sorting the medications into the various drawers and reviewing patient medication information prior to making their rounds. Because of the involvement of nurses in preparing the contents of the respective drawers, mistakes in medication dosages and amounts are made.

While the above-described computerized medication dispensing carts improve the availability and recordation of patient medication information while the nurses are making their rounds, such carts fail to sufficiently automate the drug dispensing function and often still require nursing personnel to sort medications for each patient into separate drawers and determine the prescribed dosages for each patient prior to making their rounds.

In addition to the computerized medication dispensing carts of the prior art, the prior art discloses various types of automated drug dispensing systems. U.S. Pat. Nos. 4,847,764 and 5,713,485 are illustrative. U.S. Pat. No. 4,847,764 discloses a system for dispensing medications in a medical facility that dispenses medications from floor stocks in response to orders directly from pharmacists. Such system also contains software that identifies potentially dangerous drug interactions and controls inventory. U.S. Pat. No. 5,713,485 discloses an automated drug dispensing system which includes a cabinet adapted to store a variety of prepackaged multiple-dose pharmaceuticals in a plurality of bins for filling patient prescriptions. Each bin includes a dispenser coupled to a computer system for dispensing a packaged multiple-dose pharmaceutical in response to a dispense signal. When the package is dispensed, a code reader determines the code of the dispensed package and verifies that proper dispensing of the pharmaceutical has occurred.

The above-described computerized drug dispensing systems offer various features for improving the method of administering prescribed medications in a medical facility and for reducing its cost. However, such systems are typically cumbersome and not sufficiently mobile to permit use by nurses in the proximity of the patent's bedside while making their rounds. Such systems are directed to dispensing bulk and multiple-dose medications and fail to disclose an apparatus or method for dispensing unit-dose medications for an individual patient in response to a patient's medication information supplied by a pharmacy. Finally, such systems permit the administering nurse to access and record patient specific information relating to a patient, but fail to incorporate security features, such as locked patient drawers and alarms, found in the prior art computerized medication dispensing carts.

Thus, in view of the prior art computerized medication dispensing carts and the prior art computerized drug dispensing systems, there is a need in the industry for a computerized medication dispensing cart that can accompany nursing personnel from room to room while performing their rounds that dispenses prescribed medications in prepackaged unit dosages to patients through an automated apparatus and method in response to a computer system on the cart that stores and updates the medication information regarding each patient that is provided by a pharmacy.

SUMMARY OF THE INVENTION

The computerized medication dispensing cart of the present invention significantly reduces the costs and errors associated with medication dispensing in medical facilities and improves the security and accuracy of such medication dispensing. By greatly reducing the amount of time that nurses and other hospital personnel must devote to the administration of medication, it is an object of the present invention to free up the valuable time of such nurses and other hospital personnel to allow such staff to perform other functions necessary for patient care.

According to the present invention, prepackaged unit-dose medications that have been prescribed for a patient and authorized by a pharmacist are automatically dispensed by the computerized unit-dose medication dispensing cart of the present invention at the patient's bedside in response to a nurse's request. In routine operation of the present invention, the medication information relating to a patient is initially prepared by a pharmacist in response to an order received from the patient's physician. The medication information developed for a patient by the pharmacist may include the patient's allergies, physician, date of birth, diagnoses, billing information as well as a list of the current medication orders that have been previously issued for that patient. The pharmacist reviews the patient's medication information in the pharmacist's computer system and checks the medication to be administered to the patient for drug-drug interactions with previously prescribed medications. In the event of a drug-drug interaction or dose that appears improper, the pharmacist may contact the patient's physician to verify the order. Upon verification, the pharmacist will continue with the dispensing of the prescribed dose or medication according to the present invention. The medication information for each patient that is stored in the pharmacist's computer system is continuously updated by the pharmacist.

The computerized unit-dose medication dispensing cart of the present invention is sufficiently mobile to permit nurses to roll the cart from room to room while making their rounds. The cart has a computer system which employs a central processing unit and databases that permit the nurse to access medication information relating to a particular group of patients in the round from the cart. The computer system will be menu driven in such a way that the nurse will use a touch screen monitor to input data or request medications. In alternative embodiments of the present invention, a conventional monitor, mouse and keyboard can be used to input data or request medications. The information stored in the cart's computer system will include medication information supplied by the pharmacy, proper dosing information, dangerous drug-drug interaction information and general descriptive information regarding each patient. For increased security purposes, in the preferred embodiment of the present invention, the touch screen monitor will display a digitized profile of the patient together with that patient's medication information in order to permit the nurse to verify the patient's identity prior to administering the medications. The computerized unit-dose medication dispensing cart of the present invention may also contain drawers on the cart to carry other supplies that a patient may require such as bandages and medications that cannot be dispensed by the dispensers on the cart. The medications stored in such drawers would include medications that are in a liquid form. For security purposes, such drawers can be locked. The cart also carries its own battery supply to power the computer system.

The medication information for each patient is periodically downloaded, through a modem or other conventional communication device, from the pharmacy's computer system to the computer system on the cart of the present invention. The specially designed dispensers of the cart are then preloaded with prepackaged unit-dose medications supplied by the pharmacist. This can be easily accomplished by refilling the dispenser compartment of each dispenser with a stack of the requisite prepackaged unit-dose medications or by completely replacing an empty dispenser with another full dispenser. Generally, each cart will have all necessary medications on them, and only occasionally will it be necessary to include a specialty drug on the cart. The specialty drug can either be loaded into a dispenser or can be kept in one of the plurality of conventional storage drawers on the cart.

When the nurse is in the proximity of the patient's bed and ready to administer the patient's medications, the nurse displays the patient's medication information and profile on the touch screen monitor. If the nurse verifies the identification of the patient based on the patient's profile, the nurse may then proceed with administering the medication. The computer system will display all medications due at that time for the patient for verification by the nurse. At that time, the nurse may deselect medications that have been discontinued where this has not been communicated to the pharmacy or otherwise downloaded into the computer system. The nurse will select by touching on the touch screen monitor that the medication be administered and a request signal will be transmitted to the computer system. In alternative embodiments of the present invention, the nurse may also use a conventional monitor, mouse or keyboard to initiate such a request signal.

Based on the patient medication information in the computer system or as adjusted by the nurse, the computer system in response to the request signal initiated by the nurse will automatically dispense from a plurality of dispensers on the cart the prescribed type and amount of prepackaged unit-dose medications for that patient. The cart has a separate dispenser for each prepackaged medication, and each dispenser includes a dispenser compartment having a supply of individually prepackaged unit-dose medications. All of the medications in each dispenser will be completely identified with all relevant data on the package (i.e. lot number, expiration date, name of medication, time of dispensing, etc.). There will be one unit-dose (i.e. pill) in each package. Each dispenser dispenses a single prepackaged unit dose in response to a dispense signal received from the computer system.

After each of the prepackaged medications has been dispensed from the computerized unit dose medication dispensing cart of the present invention, the nurse will tear each dispensed package from the cart and check each package's label to assure that the correct medications were dispensed. After verification of each package, the medications are administered to the patient. The computer system allows each nurse to interact with the medication information of each patient where necessary to accurately administer each medication order and to input relevant information relating to the administering of the medication. Another feature of the present invention is that each dispenser is equipped with a detector that detects when each prepackaged unit-dose medication is dispensed from the cart. The computer system will automatically enter the time and amount of the medication that was dispensed to the patient into the patient's medication information. The nurse may also input other information into the patient's records to reflect other supplies and medications that were administered to the patient, but were not dispensed from a dispenser. The information updated in the computer system includes billing as well as documentation information.

Another feature of the present invention is that in the event of an emergency the nurse may administer emergency dosages of medications that are not contained in the patient's current medication information. The nurse will select the desired medication from the touch screen monitor. If the computer system detects a drug-drug interaction, the nurse will call the pharmacy to obtain an override code to bypass the interaction objection. If no drug-drug interaction is detected or the interaction objection is bypassed, the medication can then be dispensed in accordance with the present invention. The computer system will record in the patient's medication information that an emergency dose of medication was dispensed for the patient and the override code used by the nurse to document the pharmacist and nurse dispensing such medication.

Periodically, the nurse puts the computer system of the cart in communication with the computer system of the pharmacy whereby the medication information regarding the patient in the computer system's databases are updated and revised. The link that is established with the pharmacy is a two-way link over a conventional modem or other communication device. The pharmacy is able to update patient databases and the information regarding the time and date of dispensing the medication and other billing information is supplied to the pharmacy. In this way, the nurse will have updated information regarding each patient. The power supply on the cart may also be recharged during this time.

The computer system maintains a perpetual inventory of medications in each dispenser. When the supply of a particular medication reaches a predetermined level, such information is communicated to the nurse through the touch screen monitor and also communicated to the pharmacy through the communication connection with the pharmacy. The pharmacy then replaces the empty dispenser or replaces the medication packages to refill the stack of unit-dose packages in the dispenser compartment. Furthermore, the computer system will monitor the battery power and will notify the nurse through the touch screen monitor when the battery needs recharging.

These and other features and advantages of the present invention will become apparent from the following detailed description, the accompanying drawings and the appended claims.

DETAILED DESCRIPTION OF THE PREFERRED EMBODIMENT

Figure 1:
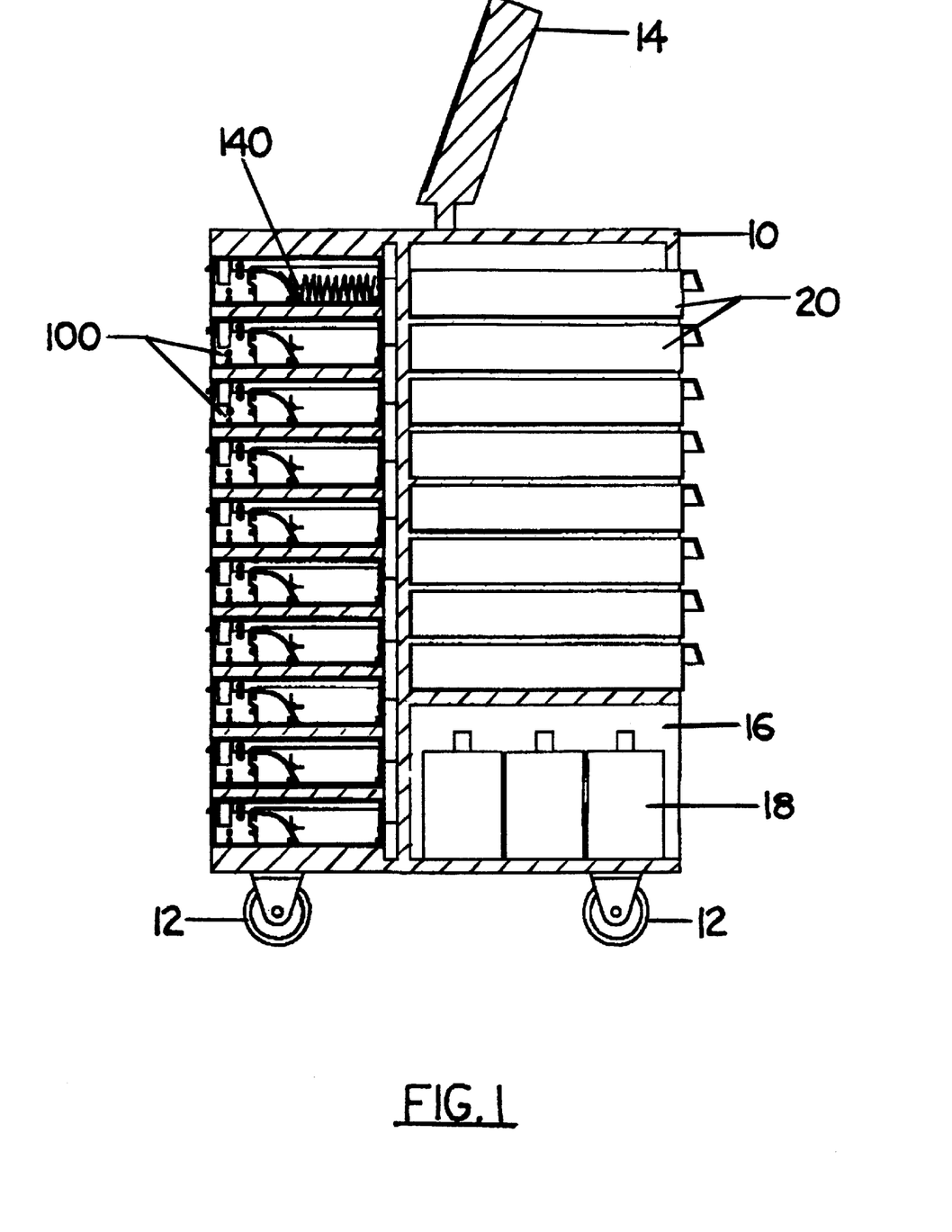
FIG. 1 is a side view of the computerized unit dose medication dispensing cart of the present invention.

FIGS. 1–6 illustrate the preferred embodiment of the apparatus and method of the present invention. As shown in FIG. 1, the computerized unit dose medication dispensing cart of the present invention includes a cart 10 that includes a plurality of wheels 12 mounted to the cart 10 which permit transport of the cart 10 from room to room by a nurse while making patient rounds. The cart 10 further includes a touch screen monitor 14 mounted on the cart 10 for easy access and view by the nurse. Alternatively, the touch screen monitor 14 can be further equipped with a conventional mouse or keyboard or replaced with a conventional monitor equipped with a conventional mouse or keyboard. The cart 10 further includes a plurality of compartments 16 for receiving dispensers 100 and conventional storage drawers 20. The conventional storage drawers are used by the nurse to store bandages and other types of medical supplies as well as other medications that cannot be easily packaged such as medications in liquid form for dispensing to a patient. For security purposes, such drawers 20 may be locked. The plurality of compartments 16 also house a computer system 50 and a plurality of batteries 18 for powering the computer system 50 of the present invention.

Figure 2:
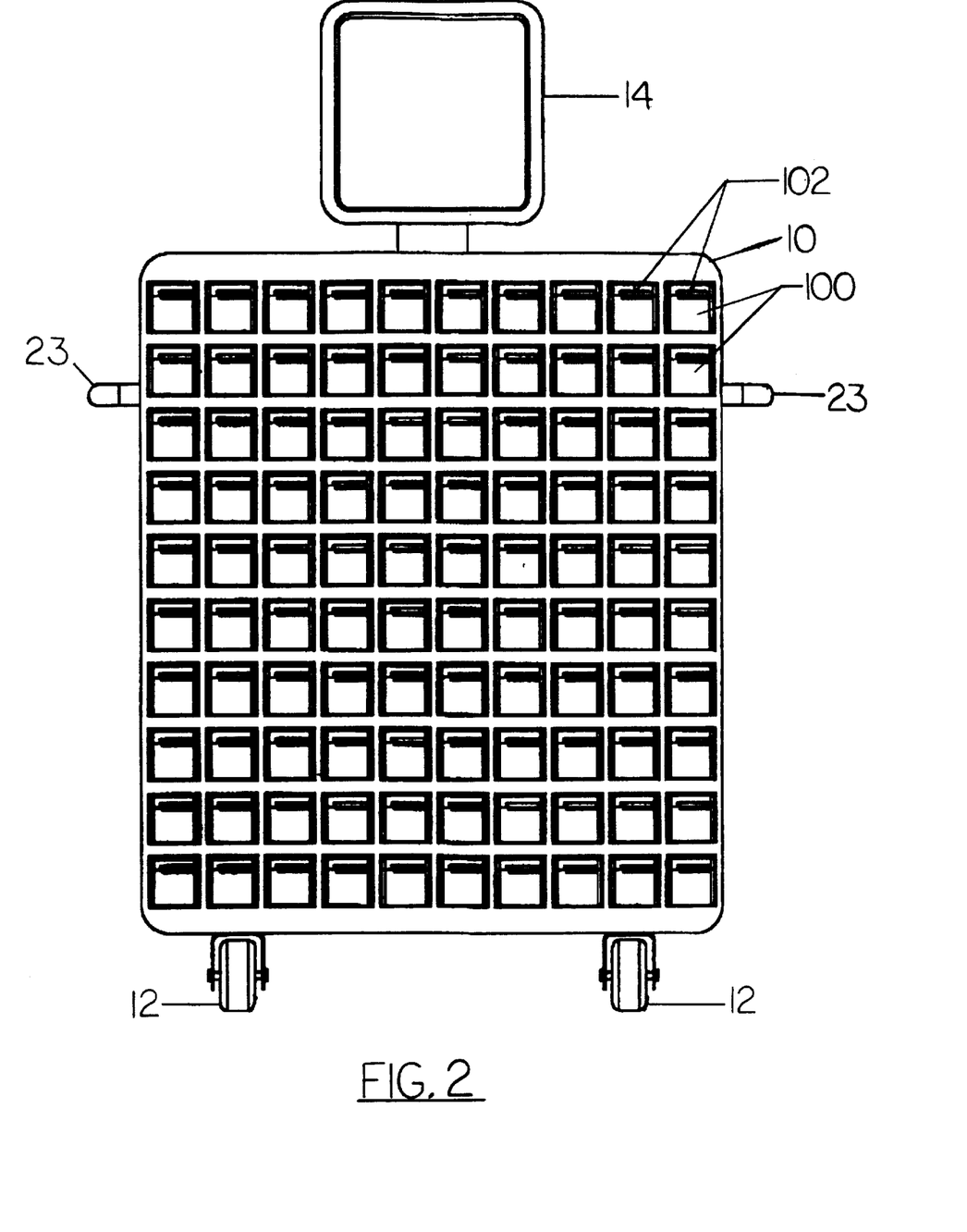
FIG. 2 is a front view of the computerized unit dose medication dispensing cart of the present invention.
Figure 3:
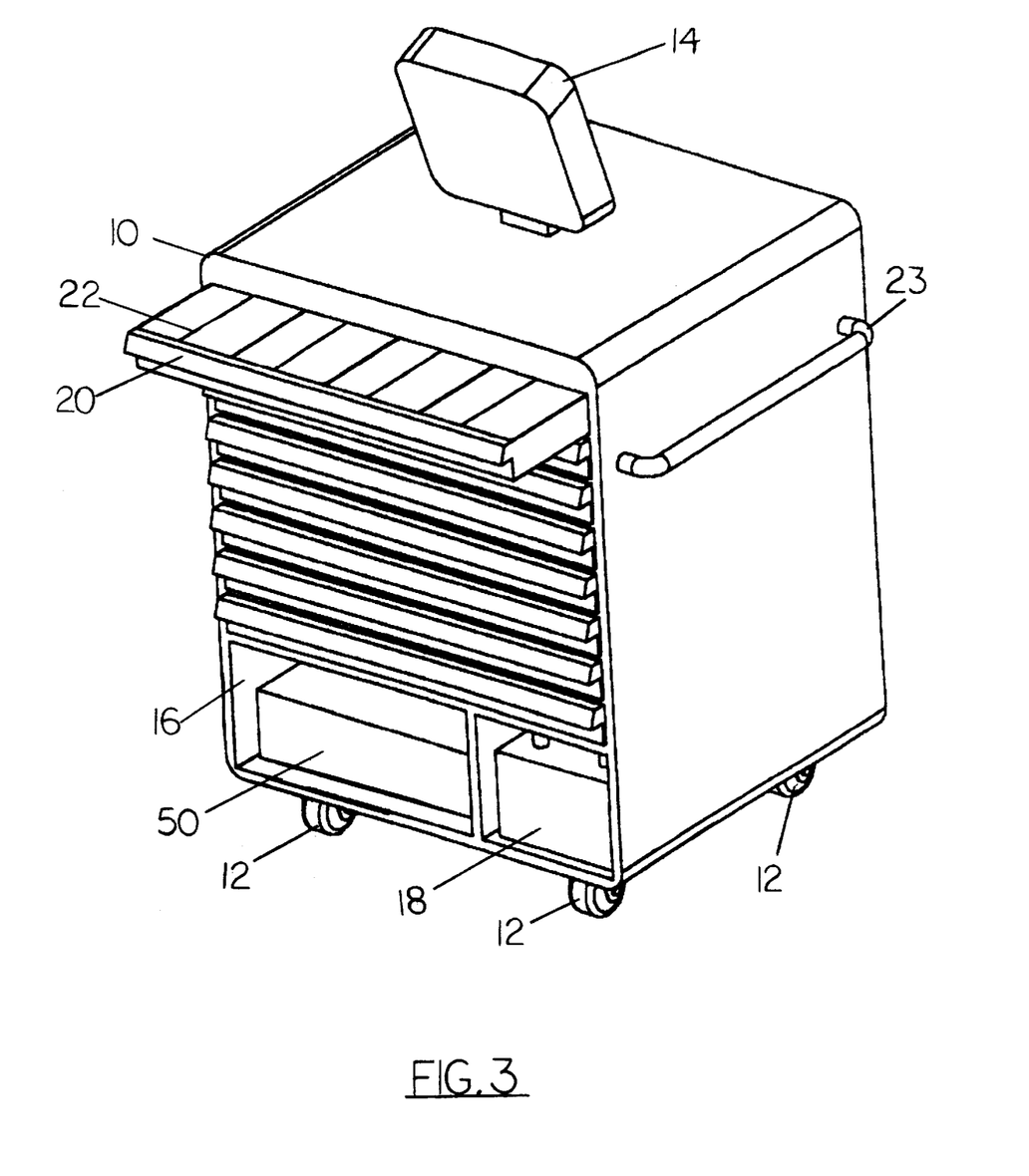
FIG. 3 is a perspective view of the computerized unit dose medication dispensing cart of the present invention.

As shown in FIG. 2, the dispensers 100 are aligned in columns and rows on the cart 10. Each dispenser 100 has a slit 102 through which a prepackaged unit dose medication is dispensed for access by the nurse. The cart 10 also includes a pair of handles 23 mounted on the cart 10 that permit the nurse to steer the cart 10 around the medical facility. As shown in FIG. 3, the computer system 50 and the plurality of batteries 18 are housed adjacent to each other in compartments 16 along the bottom of the cart 10. The storage drawers 20 contain a plurality of dividers 22 that separate the storage space in the storage drawers 20 to further assist the nurse in organizing the medical supplies and medications stored in the storage drawers 20.

The computer system 50 mounted on the cart 10 interacts with the touch screen monitor 14, and in some embodiments of the present invention, a conventional mouse or keyboard, and includes a central processing unit and memory. The computer system 50 also includes a conventional communications port that permits the computer system 50 to be plugged up to a conventional modem or other communication device in order to communicate with a pharmacy and to download information from the pharmacy. The computer system 50 is coupled separately to each dispenser 100.

Figure 4:
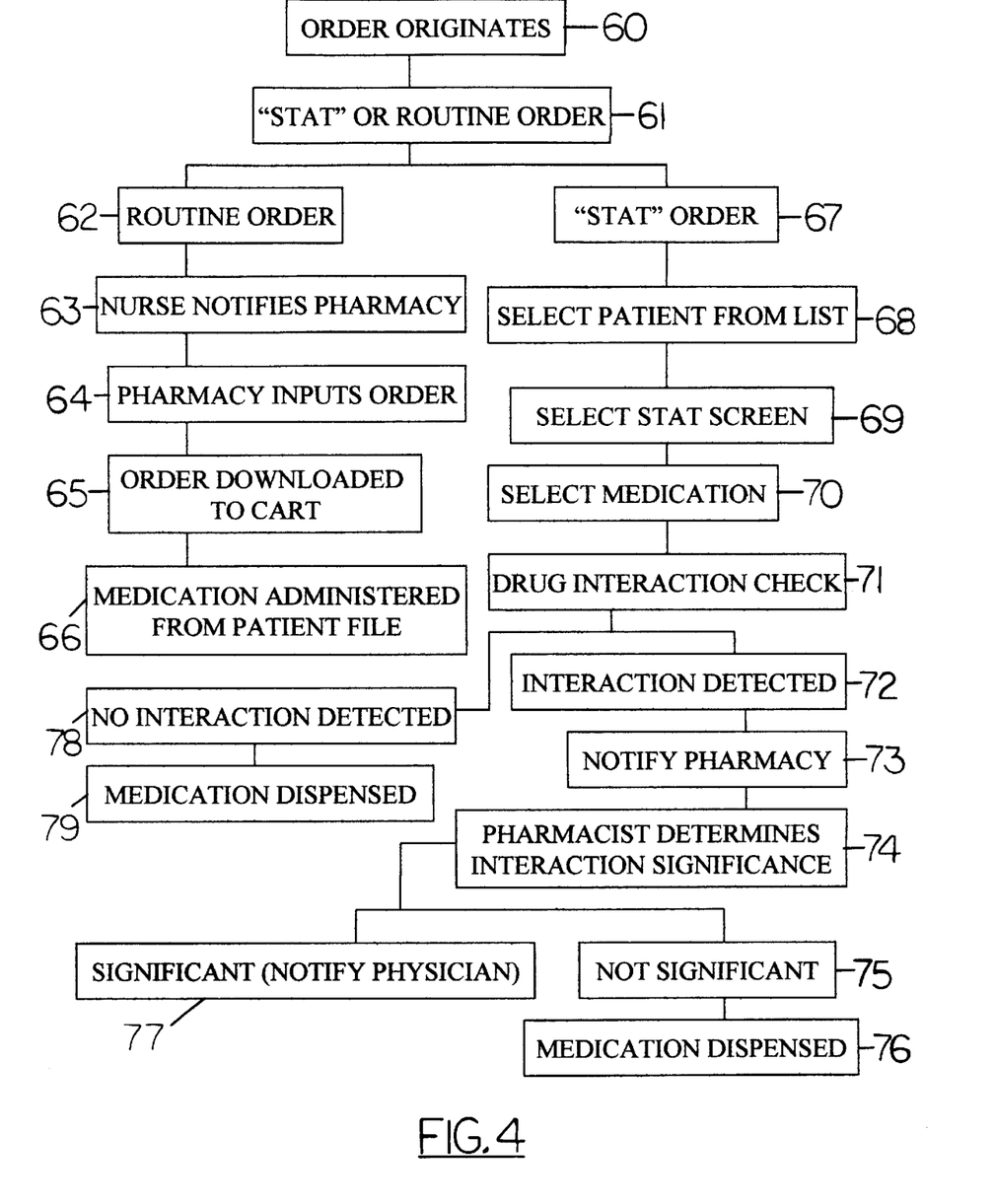
FIG. 4 is a flowchart illustrating the operational sequence for the computerized unit dose medication dispensing cart of the present invention.

The operation of the present invention will now be described with reference to the flow chart shown in FIG. 4. The computer system 50 is designed to use easy to read and manipulate displays that permit the nurse to access and update information regarding the administration of each patient's medication. The patient's physician will develop a medication order 60 for a particular medication. The nurse will then determine whether or not the order is routine or an emergency "stat" order 61. If the order is a routine order 62, the nurse will call the pharmacy to place such order with the pharmacist 63. The pharmacist will enter the information relating to such order in the pharmacy's computer system 64 to record the order and to check the medication to be administered to the patient for drug-drug interactions with previously prescribed medications. On a periodic basis, the pharmacy's computer system is connected to the computer system 50 of the present invention via a two-way link over a conventional modem or other communication device and the medication information developed by the pharmacist relating to the order is downloaded into the computer system 50 of the present invention 65. The nurse then proceeds to administer and dispense the medication from the cart 10 in a prepackaged unit dose form to each patient in accordance with the present invention 66.

In the event of an emergency situation and the issuance of a "stat" order for a medication 67, the nurse will select the patient 68 to which the medication should be administered from the patient list displayed on the touch screen monitor 14. The nurse will then select the "stat" screen 69 and select the medication 70 that needs to be administered to the patient from the medication list displayed on the touch screen monitor 14. The computer system 50 will then determine whether there is a drug-drug interaction 71 between the selected medication and previously prescribed medications to the patient. If the computer system 50 detects a drug-drug interaction 72, the nurse will call the pharmacist 73 and the pharmacist will determine whether the drug-drug interaction is significant 74. If the pharmacist determines that the drug-drug interaction is not significant 75, the nurse may proceed to administer the medication to the patient in accordance with the present invention 76. If the pharmacist determines that the drug-drug interaction is significant, the pharmacist will contact the physician to discuss the issue 77. The nurse may input an override code provided by the pharmacist to dispense the medication, and the computer system 50 will record that an emergency dose of medication was dispensed for the patient and the override code used by the nurse to document the pharmacist and nurse dispensing such medication. If no drug-drug interaction is detected 78, the medication will be dispensed 79 and the nurse proceeds with administering the medication to the patient in accordance with the present invention.

When the nurse is prepared to administer the medication from the cart 10 to the patient, the nurse displays the medication information for the patient on the touch screen monitor 14. The medication information includes various information for the nurse supplied by the pharmacy including, the patient's allergies, physician, date of birth, diagnoses and prescribed medication. A digitized profile of the patient is also displayed to assist the nurse in verifying the identification of the patient. If the nurse confirms the patient's identification, the nurse may proceed with administering the medication. The computer system 50 will display all medications due at that time for the patient for verification by the nurse. At that time, the nurse may deselect medications that have been discontinued where this has not been communicated to the pharmacy or otherwise downloaded into the computer system 50. When the nurse selects by touching on the touch screen monitor 14 that the medication be administered, a request signal is generated and communicated to the computer system 50. In response to a request signal, the computer system 50 generates and transmits automatically a dispense signal to one or more of the dispensers 100 depending on which prescribed medications are to be dispensed to each patient based on the medication information stored in the memory of the computer system 50. As further described below, the prepacked unitdose medications are simultaneously dispensed through the slit 102 in each dispenser 100 in response to the dispense signal transmitted from the computer system 50 to the dispenser 100. In an alternative embodiment of the present invention, the computer system 50 generates, but then may delay transmission of the dispense signal to one or more of the dispensers 100 to sequentially dispense the prescribed medications to the patient. Furthermore, the computer system 50 can send multiple dispense signals to a dispenser 100 in those circumstances where it is necessary to dispense multiple unit dosages of the same medication to a patient. Thus, if a patient has been prescribed three pills of a particular medication per round, three prepacked unit dose medications will be dispensed by the cart 10. Once all of the prepackaged unit-dose medications have been dispensed from a dispenser 100, the nurse simply tears each prepackaged medication advanced from the stack of the prepackaged unit dose medications in the dispenser 100.

Figure 5:
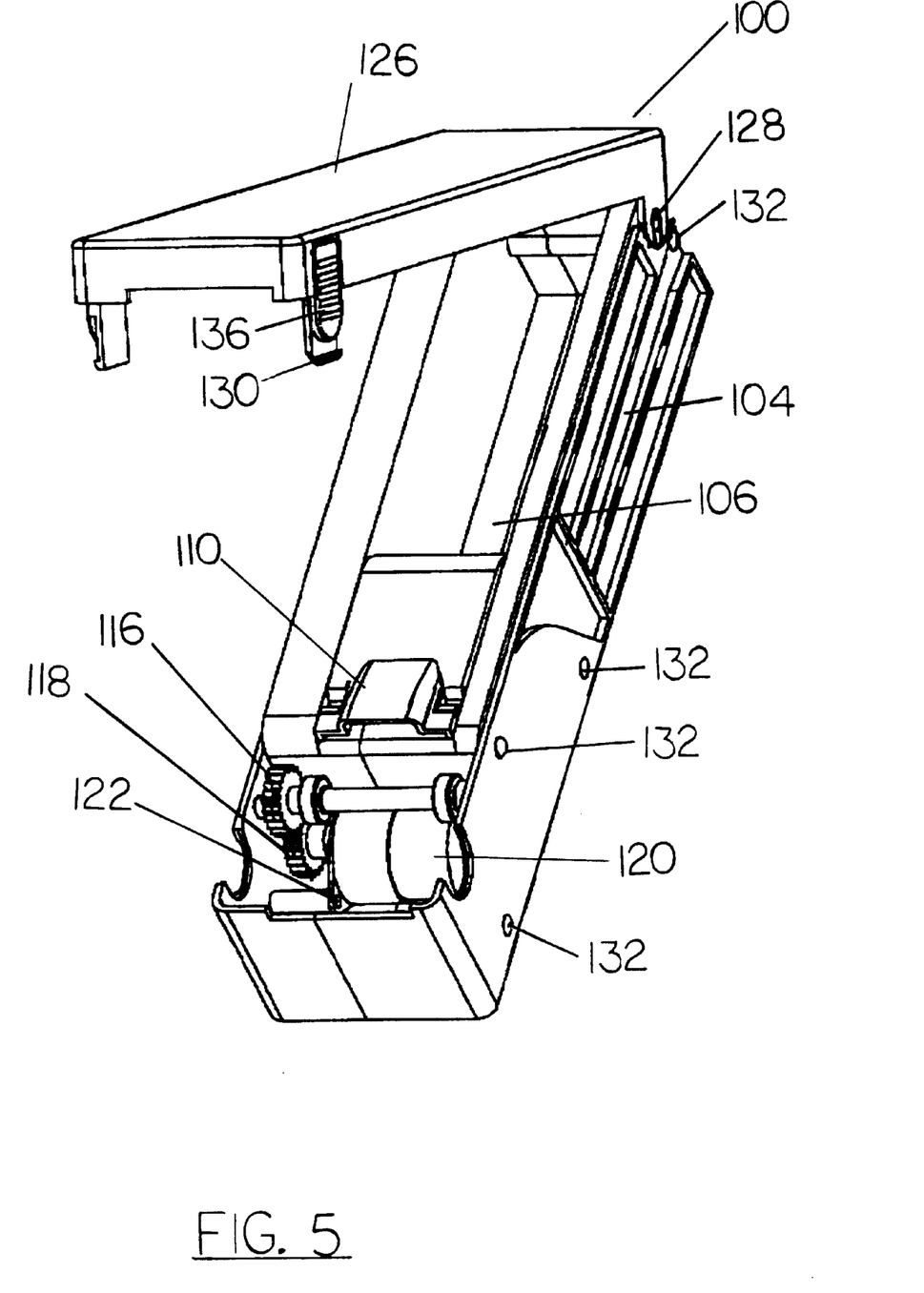
FIG. 5 is a perspective view of the dispenser of the computerized unit dose medication dispensing cart of the present invention.
Figure 6:
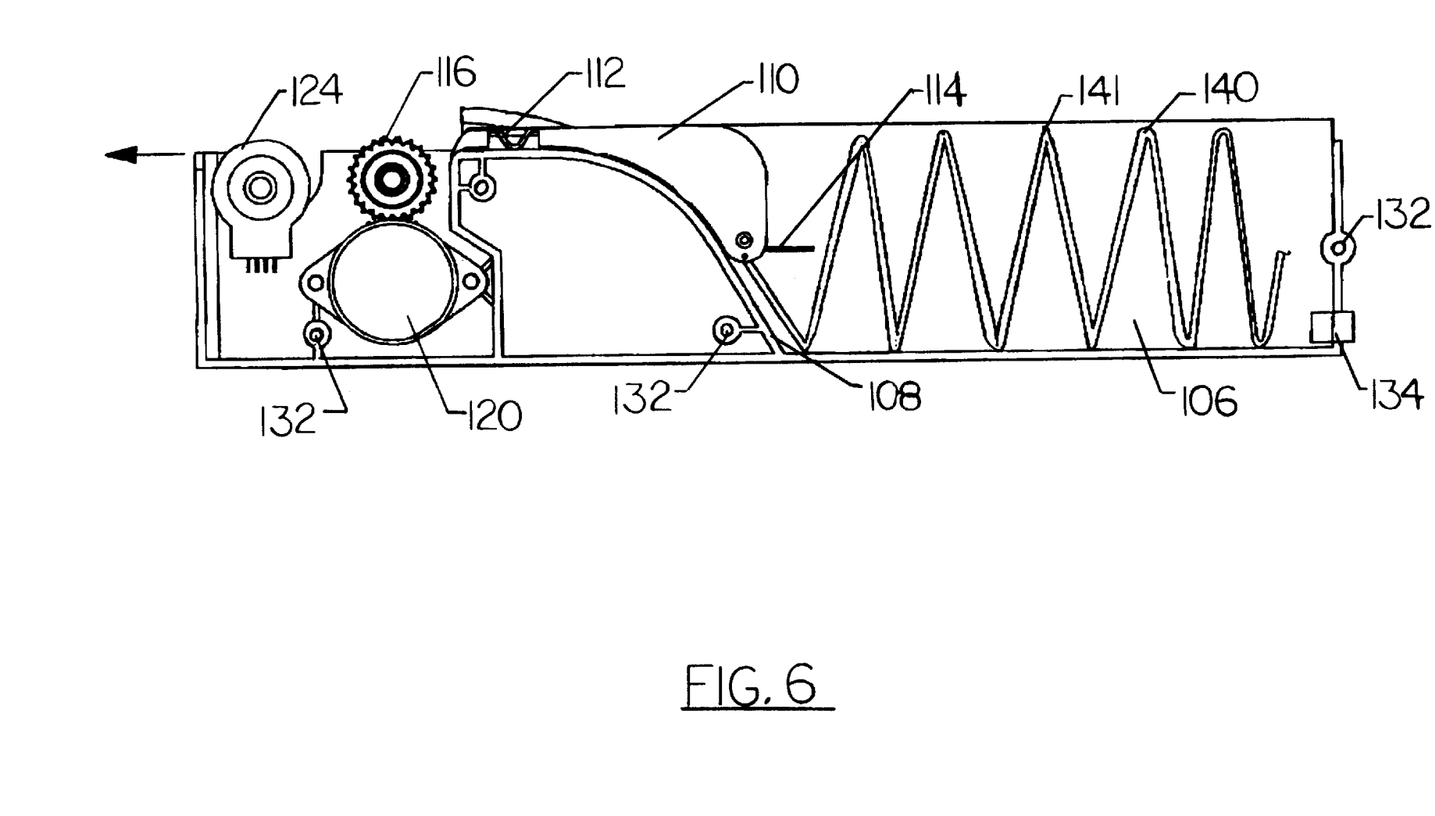
FIG. 6 is a side view of the dispenser of the computerized unit dose medication dispensing cart of the present invention.

The apparatus and method for dispensing the prepackaged unit-dose medications from each dispenser is shown in greater detail in FIGS. 5 and 6. Each dispenser 100 is inserted into the various compartments 16 of the cart 10 using track guides 104 on each side of the dispenser module. This permits the dispenser 100 to be securely mounted in the cart 10. Each dispenser 100 is designed to dispense a prepackaged unit-dose medication in response to a dispense signal received from the computer system 50. The dispenser 100 has a dispenser compartment 106 for storing a plurality of prepackaged unit dose medications in a stack 140. The prepackaged medications are folded in the stack 140, as shown in FIGS. 1 and 6, and connected at one end to each successive prepackaged medication through a conventional perforation 141. The dispenser includes a ramp 108 up which each successive package of the stack 141 of prepackaged medications advance. A clamp 110 secured by a leaf-spring 112 guides each successive package of the stack 140 out of the dispenser compartment 106 positioned to be dispensed through the dispenser module slit 102. The leaf-spring 112 is secured at one end to the clamp 110 and at the other end at a recess 114 in the wall of the dispenser 100. The dispenser 100 also includes a first roller 116 and a second roller 118 coupled to a motor 120. A motor mounting plate 122 secures the motor 120 to the dispenser 100.

The dispenser 100 has a connector 134 in the rear wall in electrical communication with the computer system 50. When a dispense signal is received from the computer system 50 through the connector 134, the motor 120 rotates the second roller 118 which rotates the first roller 116 to cause a single pre-packed medication to be advanced out of the slit 102. The pre-packaged medications advance up the ramp 108 and over the first roller 116. The motor 120 rotates the second roller 118 which rotated the first roller 116 for only that period of time to permit a single pre-packaged medication to be dispensed out of the slit 102 to permit a nurse to tear it from the dispenser 100 at the perforation 141. This same process may be performed simultaneously in all of the dispensers 100 that receive a dispense signal from the computer system 50. Thus, the desired pre-packaged unit dose medications for a patient may all be dispensed from the cart 10 at the same time permitting the nurse to administer them at once.

In those circumstances where a multiple number of a single prepackaged unit dose medications are to be dispensed from the same dispenser 100, the computer system 50 will send multiple dispense signals to the dispenser 100 holding the medication such that the motor 120 performs multiple rotation cycles. Thus, the motor 120 will complete the requisite number of rotation cycles in order to permit the desired number of prepackaged unit dose medications to be dispensed through the slit 102.

A detector 124 is positioned adjacent to the first roller 116 to detect the dispensing of each pre-packaged unit dose medication from the dispenser 100 and to send a signal to the computer system 50 verifying that dispensing of the medication has occurred. The computer system 50 then records the time and date that the medication was administered, and makes such information available to the pharmacy when the computer system 50 for the pharmacy is connected to the computer system 50 on the cart 10. The computer system 50 also documents such information as whether the medication was dispensed pursuant to a routine order and the number of dosages of the medication administered. In those cases where the medication administered is a psychotropic drug or a PRN ("as needed") drug, the computer system 50 permits the nurse to input data relating to the reaction of the patient to the administration of the psychotropic drug or PRN drug.

Finally, the dispenser 100 has a lid 126 hinged to the rear portion of the dispenser 100 at a pivot 128. The lid 126 permits the nurse or the pharmacy to insert an additional stack 140 of pre-packaged unit dose medications when the previous stack 140 is used up. On each side of the frontal portion of the lid 126 is a downwardly projecting latch 130 for engaging the inner side walls of the dispenser 100. A button 136 on the downwardly projecting latch 130 permits the opening of the lid 126 by pressing and releasing the downwardly projecting latch 130. On the outer casing of the dispenser 100 is a plurality of screw bosses 132.

Although a preferred embodiment of the invention has been illustrated in the accompanying Drawings and described in the foregoing Detailed Description, it will be understood that the invention is not limited to the embodiment disclosed but is capable of numerous modifications without departing from the scope of the invention as claimed.

What is claimed is:

1. A computerized unit dose medication dispensing cart for use in a medical facility comprising:

a cart for transporting prepackaged unit dose medications;

an input device mounted on said cart for generating a request signal to initiate the dispensing of the prepackaged unit dose medications for a patient;

a computer system mounted on said cart and coupled to the input device, the computer system having memory means for storing medication information relating to the patient and means for generating a dispense signal in response to the request signal;

a plurality of dispensing means mounted on said cart and coupled to said computer system, each dispensing means including a motor coupled to a plurality of rollers, the motor rotating the rollers in response to the dispense signal from said computer system, the rollers advancing a prepackaged unit dosage of a medication over the rollers and through a slit in the dispensing means from a stack of prepackaged unit dose medications stored in the dispensing means, each prepackaged unit dose medication dispensed through the slit being separable from the stack, said computer system transmitting the dispense signal only to the dispensing means dispensing a prepackaged unit dosage of a medication to be dispensed to the patient based on the medication information relating to the patient stored in said memory means; and detection means mounted on said dispensing means and coupled to said computer system for detecting the dispensing of the prepackaged unit dose medications from said dispensing means, the computer system recording in the memory means that the dispensing of the prepackaged unit dose medication to the patient has occurred.

2. The computerized unit-dose medication dispensing cart of claim 1 wherein said plurality of dispensing means further comprises means for simultaneously dispensing a prepackaged unit dosage of each of the medications ordered for a patient from a pharmacy for administering by a nurse to a patient while the nurse is making rounds.

3. The computerized unit-dose medication dispensing cart of claim 1 wherein said plurality of dispensing means further comprises means for sequentially dispensing a prepackaged unit dosage of each of the medications ordered for a patient from a pharmacy for administering by a nurse to a patient while the nurse is making rounds.

4. The computerized unit-dose medication dispensing cart of claim 1 wherein said input device comprises a touch screen monitor.

5. The computerized unit-dose medication dispensing cart of claim 4 wherein said input device displays a digitized profile of each patient with the medication information of the patient to assist the nurse in verifying the identification of the patient.

6. The computerized unit-dose medication dispensing cart of claim 1 wherein said input device comprises a display monitor equipped with a mouse.

7. The computerized unit-dose medication dispensing cart of claim 1 wherein said input device comprises a display monitor equipped with a keyboard.

8. The computerized unit-dose medication dispensing cart of claim 1 wherein said computer system further comprises a communications port for connecting a modem to establish a two-way link with a pharmacy to transmit and receive medication information relating to a patient.

9. The computerized unit-dose medication dispensing cart of claim 1 wherein said computer system further comprises means for recording in the memory means information input by a nurse into the input device relating to a patient's reaction to the administering of a medication.

10. The computerized unit-dose medication dispensing cart of claim 1 wherein said cart further comprises a plurality of storage drawers for storing medical supplies and medications that cannot be dispensed by said dispensing means.

11. A method for dispensing prepackaged unit-dose medications to a patient for use in a medical facility comprising:

transporting prepackaged unit-dose medications on a cart;

storing medication information relating to the patient in a computer system mounted on said cart;

generating a request signal to initiate the dispensing of prepackaged unit-dose medications for the patient from an input device mounted on said cart;

receiving the request signal at said computer system;

generating a dispense signal at said computer system in response to the request signal;

transmitting the dispense signal from said computer system to a plurality of dispensers storing a plurality of prepackaged unit dosages of a medication to be dispensed to the patient;

receiving the dispense signal at each of said plurality of dispensers;

rotating a plurality of rollers located within each of said plurality of dispensers in response to the dispense signal to advance a prepackaged unit dosage of a medication over the rollers and through a slit in each dispenser from a stack of prepackaged unit dose medications stored in each dispenser; and detecting that the prepackaged unit-dose medications were dispensed from each dispenser.

12. The method of claim 11 further comprising the step of displaying a digitized profile of the patient from the input device to assist in verifying the patient's identity.

13. The method of claim 11 further comprising the step of recording information relating to a patient's reaction to the administering of a medication.

14. The method of claim 11 further comprising the step of connecting a modem to said computer system to establish a two-way link with a pharmacy.

15. The method of claim 14 further comprising the step of transmitting to the pharmacy information relating to the time and date that the prepackaged unit-dose medications were administered to the patient.

16. The method of claim 15 further comprising the step of receiving from the pharmacy information relating to medication orders developed by the pharmacist for the patient.

* * * * *